United States Patent [19]

Bartlett

[11] Patent Number: 4,534,489
[45] Date of Patent: Aug. 13, 1985

[54] BIOHAZARD WASTE CONTAINER

[76] Inventor: James V. Bartlett, 1714 Sherman Ave., Janesville, Wis. 53545

[21] Appl. No.: 609,464

[22] Filed: May 11, 1984

[51] Int. Cl.³ .......................... B65D 5/08; B65D 5/60
[52] U.S. Cl. .................................. 220/404; 206/459;
220/1 T; 220/462; 229/37 R; 229/37 E; 229/44 R; 229/45 R
[58] Field of Search ............... 220/404, 462, 1 T, 463; 229/44 R, 47, 45 R, 37 R, 37 E; 206/459

[56] References Cited

U.S. PATENT DOCUMENTS

| 940,242 | 11/1909 | Ferrall et al. | 229/47 X |
|---|---|---|---|
| 945,349 | 1/1910 | Tatham | 229/37 R |
| 1,131,135 | 3/1915 | Hudson | 229/47 |
| 1,198,032 | 9/1916 | Henze | 229/37 R |
| 1,417,790 | 5/1922 | Arntz | 229/47 X |
| 1,582,375 | 4/1926 | Bliss | 229/45 R |
| 1,926,299 | 9/1933 | Monk | 229/37 R X |
| 2,281,424 | 4/1942 | Englert | 229/8.5 |
| 2,416,332 | 2/1947 | Lehman | 229/37 R |
| 2,515,327 | 7/1950 | Bergstein | 229/44 R X |
| 2,672,273 | 3/1954 | Smith | 229/45 X |
| 3,512,699 | 5/1968 | Wilson | 229/37 R X |
| 3,539,360 | 11/1970 | Wood | 229/37 R |

Primary Examiner—Allan N. Shoop
Attorney, Agent, or Firm—Evelyn M. Sommer; William W. Jones

[57] ABSTRACT

The container is particularly adapted for use in the disposal of biohazardous waste. The container includes an outer corrugated paperboard carton in which there is disposed a plastic refuse bag. The carton includes a top cover which has side walls which overlap side walls of the carton and which is pivotally connected to the remainder of the carton for movement to a closed position. The bag is disposed in the carton with its top portion being bloused over the top of the carton. When the top cover of the carton is closed, the top of the bag is caught between the top cover side walls and the carton side walls and held in place. A pivoting access flap is formed in the top cover to allow waste material to be dropped into the bag through the flap.

7 Claims, 6 Drawing Figures

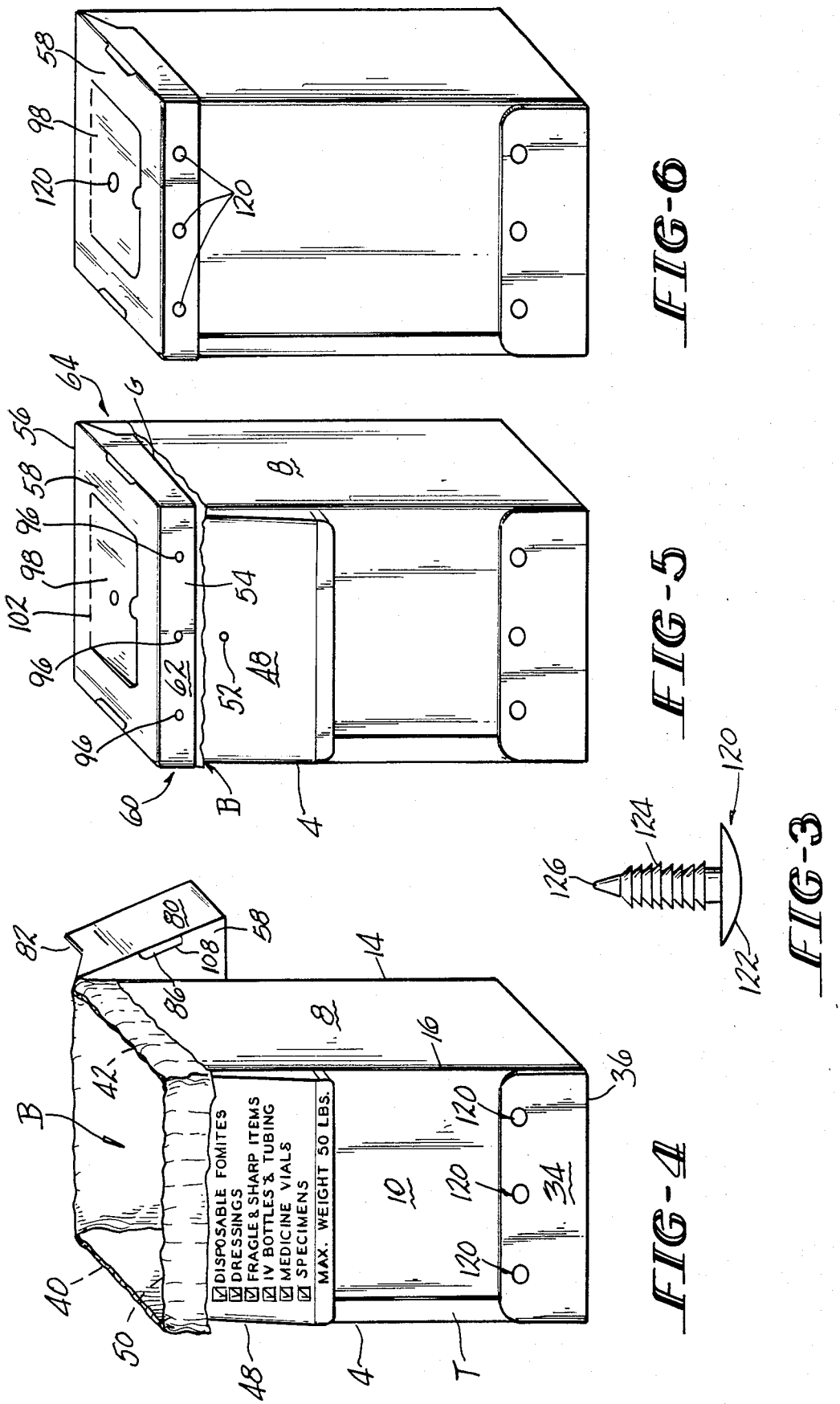

BIOHAZARD WASTE CONTAINER

This invention relates to a container for use in the disposal of biohazardous waste material of the type commonly generated in hospitals, laboratories, and the like.

The disposal of biohazardous waste, such as disposable blood supply paraphenalia, hypodermic syringes, dressings, and the like, which is generated in hospitals, laboratories, physicians' offices, and the like, is typically carried out by simply discarding the waste material in plastic bags which are generally supported in receptacles such as trash cans. When filled, the bags are closed and removed from the support receptacles and taken away for incineration, or removal from the premises. While being filled, these bags can create a disagreeable situation due to the fact that they remain open to ambient surroundings until filled. Additional problems are created after the bags are closed and removed from the support receptacle in that the bags can be punctured by any sharp materials which have been deposited in the bags.

This invention provides an improved container for use in the disposal of biohazardous waste. The container of this invention includes a carton which is formed from a one piece cut and scored corrugated paperboard blank. The inner surface may be coated with a moisture resistant material such as wax or polyethylene. The carton includes four side wall panels and a preferably four ply bottom wall construction. An inner top cover panel is foldably connected to the top edge of one of the side wall panels so that the inner top cover panel overlies the outer surface of that side wall panel when the container is being used to collect the waste material. A top cover assembly is foldably connected to the opposite one of the side wall panels and is pivotable to a closed position which closes off the top of the carton. The top cover assembly includes downwardly depending side panels which overlie the outer surfaces of each of the remaining three side wall panels of the carton. Provision is made to releasably retain the top cover assembly in its closed condition. The top wall of the top cover assembly is provided with a swinging door or flap which permits access to the interior of the carton when the top cover assembly is closed. The top wall of the top cover assembly may also be provided with a pie cut opening which also allows access to the interior of the carton when the top cover assembly is closed. One or more double strength plastic bags are disposed in the carton (if more than one bag is used, the bags will be one inside the other). The bag or bags are draped inside of the carton with the open mouth of the bag being bloused over the top edges of the side wall panels of the carton. When the top cover assembly is closed, the upper margin of the bag is caught between the side wall panels of the carton and the side panels of the top cover assembly and thereby held in place to effectively line the carton. The inside of the bag is thus accessible through the swinging door or flap for receipt of waste materials.

It is, therefore, an object of this invention to provide an improved container for the receipt and retention of biohazardous waste material and disposal by incineration or intermediate storage and transport to an authorized landfill site.

It is a further object of this invention to provide a container of the character described which includes a corrugated carton having a plastic bag lining the interior thereof.

It is yet another object of this invention to provide a container of the character described wherein the carton has a top cover assembly which holds the bag in place in the carton, which top cover assembly includes a swinging door panel which is normally biased closed but which can be swung open to allow discarding of waste material into the bag.

These and other objects and advantages of the invention will become more readily apparent from the following detailed description of a preferred embodiment of the invention when taken in conjunction with the accompanying drawings, in which:

FIG. 3 is a side elevational view of the assembly fastener used to assemble the carton formed from the blank of FIG. 1;

FIG. 4 is a perspective view of the container of this invention shown with the top cover assembly in the open position and the bag positioned inside of the carton;

FIG. 5 is a perspective view similar to FIG. 4 but showing the top cover assembly of the carton in the closed position wherein waste material can be discarded into the bag disposed in the carton; and FIG. 6 is a perspective view of the container of FIGS. 4 and 5 showing the container after it is filled with waste material and closed up for disposal.

Figure 1:
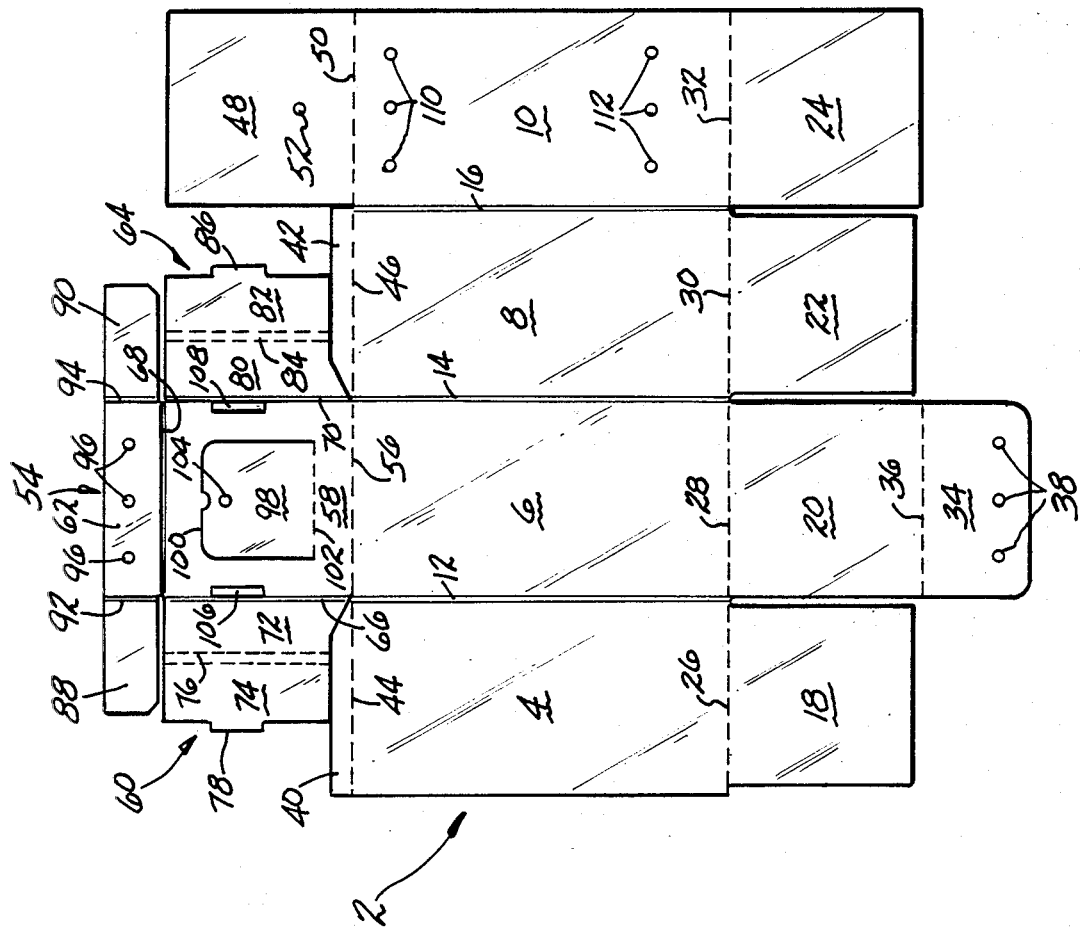
FIG. 1 is a plan view of a cut and scored corrugated paperboard blank from which a preferred embodiment of the container carton of this invention is formed.

Referring now to the drawings, there is shown in FIG. 1 a cut scored corrugated paperboard blank from which is constructed the outer carton portion of the container of this invention. The blank 2 includes a plurality of side wall panels 4, 6, 8 and 10 which are interconnected by fold lines 12, 14 and 16. Bottom wall panels 18, 20, 22 and 24 are connected to the side wall panels 4, 6, 8 and 10 by fold lines 26, 28, 30 and 32 respectively. The bottom wall panel 20 is an outermost panel on the carton and includes a securement flap 34 connected thereto by a fold line 36. The securement flap 34 has a plurality of holes or weakened areas 38 formed therein. A pair of support panels 40 and 42 are connected to the side wall panels 4 and 8 along fold lines 44 and 46 respectively. A display—inner top closure panel 48 is connected to the side wall panel 10 along a fold line 50. A hole or weakened area 52 is formed in the display—inner top closure panel 48. A top cover assembly denoted generally by the numeral 54 is connected to the side wall panel 6 by a fold line 56. The top cover assembly 54 includes a top cover panel 58 having side panels 60, 62 and 64 connected to side edges thereof along fold lines 66, 68 and 70 respectively. The side panel 60 is a compound panel having an outer component 72 and an inner component 74 interconnected by a double fold line 76. The inner component has a locking tab 78 disposed on its free edge. The side panel 64 is also a compound panel having an outer component 80 and an inner component 82 interconnected by a double fold line 84. The inner component 82 has a locking tab 86 formed on its free edge. The remaining side panel 62 has wing panels 88 and 90 connected to opposite edges thereof along fold lines 92 and 94 respectively. The side panel 62 also has a plurality of holes or weakened areas 96 formed therein. The top cover panel 58 has a pivoting or swinging door panel 98 disposed therein which is bounded by a U-shaped cut 100 and is connected to the panel 58 by a cut fold line 102. A hole or weakened area 104 is formed in the door panel 98. A pair of locking slots 106 and 108 are formed in the top cover panel 58 adjacent to the fold lines 66 and 70 respectively. The side wall panel 10 has a first set of holes or weakened areas 110 formed therein near the fold line 50, and a second set of holes or weakened areas 112 formed therein near the fold line 32.

Figure 2:
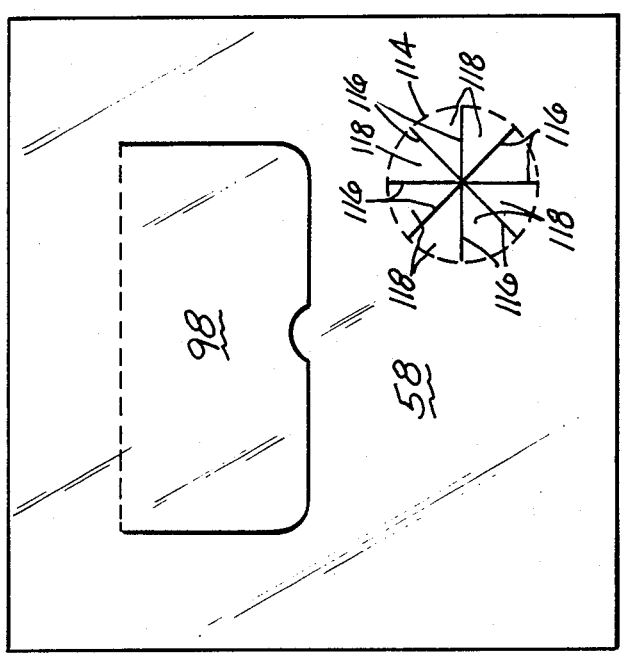
FIG. 2 is an enlarged plan view of a modified form of the top panel of the top cover assembly of the carton blank of FIG. 1.

Referring to FIG. 2, a modified form of the top cover panel 58 is shown. In addition to the swinging door panel 98, there is also included an additional access passage formed from a circular score line 114 combined with a plurality of diagonal cuts 116 which form a plurality of deflectable flaps 118, which access passage can be termed a "pie cut" opening. This access opening can be used to discard various items, such as syringes, sample tubes, and the like smaller paraphenalia, into the container.

Referring to FIG. 3, there is shown a carton assembly fastener which is used to assemble the blank 2 into the carton. The fastener, denoted generally by the numeral 120 includes an enlarged head portion 122 and a barbed shank portion 124. The shank 124 is provided with a rounded end 126. The fastener is preferably formed from molded plastic and is used to retain certain of the carton panels in place, as will be described in greater detail hereinafter.

Referring now to FIG. 4, the carton is shown in its erected condition. The carton is erected by folding the blank 2 about fold lines 12, 14, and 16 to form a rectangular tubular body from the side wall panels 4, 6, 8, and 10. A strip of tape T is then used to join the side walls 4 and 10 together. This will form a flattened bulk shipping and storage configuration for the carton. Further erecting of the carton is accomplished by squaring off the side wall panels 4, 6, 8 and 10 and folding the bottom wall panels 18, 22 and 24 into overlapping relationship. The outer bottom wall panel 20 is then folded so as to overlap the panels 18, 22 and 24, and the securement flap 34 is then folded into face-to-face contact with the side wall panel 10. This brings the holes 38 and 112 in the flap 34 and panel 10 respectively into alignment whereupon an assembly fastener 120 is pushed through each of the aligned sets of holes 38 and 112 to secure the flap 34 to the side wall panel 10. The display—inner top closure panel 48 is folded about the fold line 50 so as to overlie the outer surface of the side wall panel 10. The visible surface of the panel 48 is printed with a listing of items which may be discarded into the container, as shown in FIG. 4. The opposite side of the panel 48 is printed with assembly instructions for the carton. The top cover assembly is erected by folding the side panel 62 about fold line 68 and folding wing panels 88 and 90 about fold lines 92 and 94 respectively to underlie fold lines 66 and 70 respectively. Outer side panels 72 and 80 are then folded about fold lines 66 and 70 and inner side panels 74 and 82 are folded about double fold lines 76 and 84 so that wing panels 88 and 90 are sandwiched between panels 72 and 74, and 80 and 82 respectively. Lock tabs 78 and 86 are inserted into lock slots 106 and 108 respectively to lock the top cover assembly in its erected position. The support panels 40 and 42 are folded inwardly about their respective fold lines 44 and 46. The bag B is then inserted into the open carton and the top of the bag is bloused over the tops of the side wall panels 4, 8, and 10, as shown in FIG. 4.

The top cover assembly is then pivoted about the fold line 56 so as to bring the side panel assemblies 54, 60 and 64 into overlying relationship with the display—inner top closure panel 48, the side wall panel 4 and the side wall panel 8. The bloused portions of the bag B are thus held in place between the overlapping portions of the carton. In the closed condition shown in FIG. 5, the side wall assemblies 60 and 64, by reason of the double fold lines 76 and 84, provide hand grips at G whereby the container can be moved about while remaining closed. When the container is thus closed, the swinging door panel 98 in the top cover panel 58 overlies the open mouth of the bag B whereby waste material can be discarded into the bag B via the swinging door panel 98. During use of the container to receive waste material, the fold line 102 tends to bias the swinging door panel 98 to the closed position, as shown in FIG. 5, whereby the ambient surroundings are protected from the material which has been discarded into the container.

When the container is full and the top cover assembly is opened, the bag is tied closed with a tie which is provided. All of the tied up bag is tucked inside of the carton and the display—inner top closure panel 48 is pivoted about the fold line 50 into overlying relationship with the support panels 40 and 42. The top cover assembly is then returned to its closed position overlying the display—inner top closure panel 48. Fastener pins 120, of the type shown in FIG. 3, are inserted through the aligned holes 96 and 110 to secure the top cover assembly in place. A fastening pin 120 is also inserted through the aligned holes 104 and 52 in the swinging door panel 98 and the underlying display—inner top closure panel 48 to lock the swinging door panel 98 in the plane of the remainder of the top cover panel 58. In the condition shown in FIG. 6, the container is ready to be ultimately disposed of.

It will be understood that the container is provided in its flattened, knock down condition with the necessary bag, fastening pins, tie, and the like. The carton preferably has a clay white exterior which can be printed and a moisture resistant coated interior.

The container of this invention provides a safe depository for biohazardous waste material wherein the discarded material is shielded from the ambient surroundings. The use of the outer corrugated paperboard carton allows the container to be moved about with no problems and allows the entire container to be discarded when full without having to remove the bag from the carton. The display—inner closure panel provides means for locking the swinging panel in place in a closed position when the container is to be ultimately discarded. The fastening pins allow the use of relatively heavy duty corrugated board for the carton and, yet, permit the carton to be quickly and securely erected. It will be appreciated that this invention provides a safe, sturdy, mobile and, yet, completely disposable waste container which is particularly suited for use in hospitals, clinics, laboratories and other locations which produce biohazardous waste material. The same container design, with changes in labeling and interior bag, can also be used for the temporary storage and transport of low level radioactive wastes generated by hospital nuclear medicine departments.

Since many changes and variations of the disclosed embodiment of the invention may be made without departing from the inventive concept, it is not intended to limit the invention otherwise than as required by the appended claims.

What is claimed is:

1. A carton for containment of waste material, said carton being formed from a unitary corrugated paperboard blank, and said carton comprising:
   (a) a plurality of side wall panels hingedly connected together to form a tubular body;
   (b) a plurality of bottom wall panels foldably connected to bottom edges of said side wall panels and overlappingly disposed to form a multi-ply bottom for said carton;
   (c) a top cover assembly foldably connected to a top edge of one of said side wall panels, said top cover assembly including a plurality of side panels operative to overlie upper portions of said side wall panels when said top cover assembly is in a closed position, and said top cover assembly further including a top wall extending between said side panels to close the top of said carton when said top cover assembly is in said closed position;
   (d) a swinging door panel formed within said top wall and pivotally connected thereto to allow access therethrough to the interior of said carton;
   (e) a display—inner top closure panel pivotally connected to a top edge of a second one of said side wall panels, said display—inner top closure panel being pivotable between a first position overlying an outside surface of said second side wall panel and a second position underlying said top wall when said top cover assembly is in said closed position; and
   (f) means for securing said swinging door panel to said display—inner top closure panel when the latter is in said second position.

2. The carton of claim 1 further comprising support panels foldably connected to upper edges of side wall panels flanking said second side wall panel, said support panels underlying said display—inner top closure panel when the latter is in said second position to prevent said display—inner top closure panel from deflecting into the interior of said carton.

3. The carton of claim 1 wherein said means for securing comprises aligned openings in said swinging door panel and said display—inner top closure panel and a fastener pin having an enlarged head and a barbed shank, said fastener pin being inserted through said aligned openings.

4. The carton of claim 1, wherein an opposed pair of said top cover assembly side panels comprise outer and inner components foldably connected together along a double fold line to form two-ply hand grip means for moving said carton.

5. The carton of claim 1 wherein one of said top cover assembly side panels includes a plurality of holes formed therein in alignment with a plurality of similar holes formed in an underlying one of said side wall panels and a plurality of fastening pins having enlarged heads and barbed shanks, said pins being operable to secure said top cover assembly in said closed position by being inserted through aligned pairs of said holes.

6. The carton of claim 1 wherein said bottom wall panels include an outer bottom wall panel having a securement flap foldably connected thereto, said securement flap overlying an outer surface of a predetermined side wall panel, said securement flap having a plurality of holes formed therein which are aligned with a plurality of similar holes formed in said predetermined side wall panel, and further comprising a plurality of fastening pins having enlarged heads and barbed shanks, said pins being inserted through aligned pairs of said holes to fasten said securement flap to said predetermined panel.

7. The carton of claim 1 in combination with a heavy duty plastic bag, said bag being disposed in said carton and having upper marginal edges bloused over top portions of said side wall panels and held in place by said side panels of said top cover assembly when the latter is in said closed position.

* * * * *